US00PP31352P2

(12) United States Plant Patent
Eveleens

(10) Patent No.: US PP31,352 P2
(45) Date of Patent: Jan. 14, 2020

(54) ***HYDRANGEA* PLANT NAMED 'HORTMAVI'**

(50) Latin Name: *Hydrangea macrophylla*
Varietal Denomination: Hortmavi

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL); KOUSTER HOLDING B.V., Boskoop (NL)

( * ) Notice: Subject to any disclaimer, the term of this patent is extended or adjusted under 35 U.S.C. 154(b) by 0 days.

(21) Appl. No.: 15/999,948

(22) Filed: Aug. 30, 2018

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ... A01H 5/02; A01H 5/00; A01H 1/02; A01H 6/48; A01H 6/00
See application file for complete search history.

(56) References Cited

PUBLICATIONS

Berger 2018 Gardens Design Online New Plants 2018, retrieved on Jun. 12, 2019, retrieved from the Internet at https://www.gardendesignonline.com/gardendesignonline/2018/01/new-plants-2018-i.html, one page. (Year: 2018).*

* cited by examiner

*Primary Examiner* — June Hwu
(74) *Attorney, Agent, or Firm* — Penny J. Aguirre

(57) ABSTRACT

A new cultivar of *Hydrangea macrophylla* plant named 'Hortmavi' that is characterized by its exhibits mophead inflorescences that are uniformly globular in shape and dark pink in color, its sturdy thick textured sterile flowers, its compact and uniform plant habit, and its suitability as a potted plant.

2 Drawing Sheets

Botanical classification: *Hydrangea macrophylla.*
Varietal denomination: 'Hortmavi'.

CROSS REFERENCE TO RELATED APPLICATIONS

This application is co-pending with a U.S. Plant patent Application filed for a plant derived from the same breeding program that are entitled *Hydrangea* Plant Named 'Horthat' (U.S. Plant patent application Ser. No. 15/999,956), 'Hortmagitri' (U.S. Plant Pat. No. 30,044), and 'Kolmaru' (U.S. Plant Pat. No. 25,104).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings on monrovia.com and plantsnouveau.com.

BACKGROUND OF THE INVENTION

The present invention relates to a new and distinct cultivar of *Hydrangea macrophylla* and will be referred to hereafter by its cultivar name, 'Hortmavi'. 'Hortmavi' represents a new mophead type *Hydrangea*, a deciduous shrub grown for use as a landscape plant and as a cut flower.

The new cultivar was derived from an ongoing controlled breeding program conducted by the Inventor in Boskoop, The Netherlands. An objective of the breeding program included developing a new cultivar of *Hydrangea* with flowers that are dark pink in color combined with other desirable straits. 'Hortmavi' was derived from a cross made in April of 2006 between proprietary plants from the Inventor's breeding program reference no. 03-027-03 (not patented) as the female parent and reference no. 01-044-13 (not patented) as the male parent. 'Hortmavi' was selected in August of 2016 as a single unique plant from amongst the resulting seedlings.

Asexual propagation of the new cultivar was first accomplished by stem cuttings in Boskoop, The Netherlands by the Inventor in August of 2008. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortmavi' as a unique cultivar of *Hydrangea.*

1. 'Hortmavi' exhibits mophead inflorescences that are uniformly globular in shape and dark pink in color.

2. 'Hortmavi' exhibits sturdy thick textured sterile flowers.
3. 'Hortmavi' exhibits a compact and uniform plant habit.
4. 'Hortmavi' exhibits suitability as a potted plant.

The female parent of 'Hortmavi' differs from 'Hortmavi' in having less inflorescences with sterile sepals that are lighter in color that tend to turn downwards as they mature, and in having less branching. The male parent of 'Hortmavi', differs from 'Hortmavi' in having less sterile flowers with sepals that are darker pink in color. 'Hortmavi' can be most closely compared to the *Hydrangea* cultivars 'Kolmaru', 'Hortmagitri', and 'Horthat'. 'Kolmaru' is similar to 'Hortmavi' in inflorescence shape but differs from 'Hortmavi' in having sterile flower sepals that are dark red in color and slightly less sturdy in texture and in having larger inflorescences. Hortmagitri' is similar to 'Hortmavi' in inflorescence shape and in having sepals with a sturdy texture but differs from 'Hortmavi' in having sterile flowers with sepals that are darker in color and flushed with darker red. 'Horthat' is similar in plant habit and Inflorescence shape, and in having sturdy sterile flower sepals. 'Horthat' differs in having smaller inflorescences that are dark rose in color.

BRIEF DESCRIPTION OF THE DRAWINGS

The accompanying colored photographs illustrate the overall appearance and distinct characteristics of the new *Hydrangea*. The photographs were taken of a two-year-old plant of 'Hortmavi' as grown in a greenhouse in 3-gallon containers in Visalia, Calif.

The photograph in FIG. 1 provides a side view of 'Hortmavi' in bloom.

Figure 1:
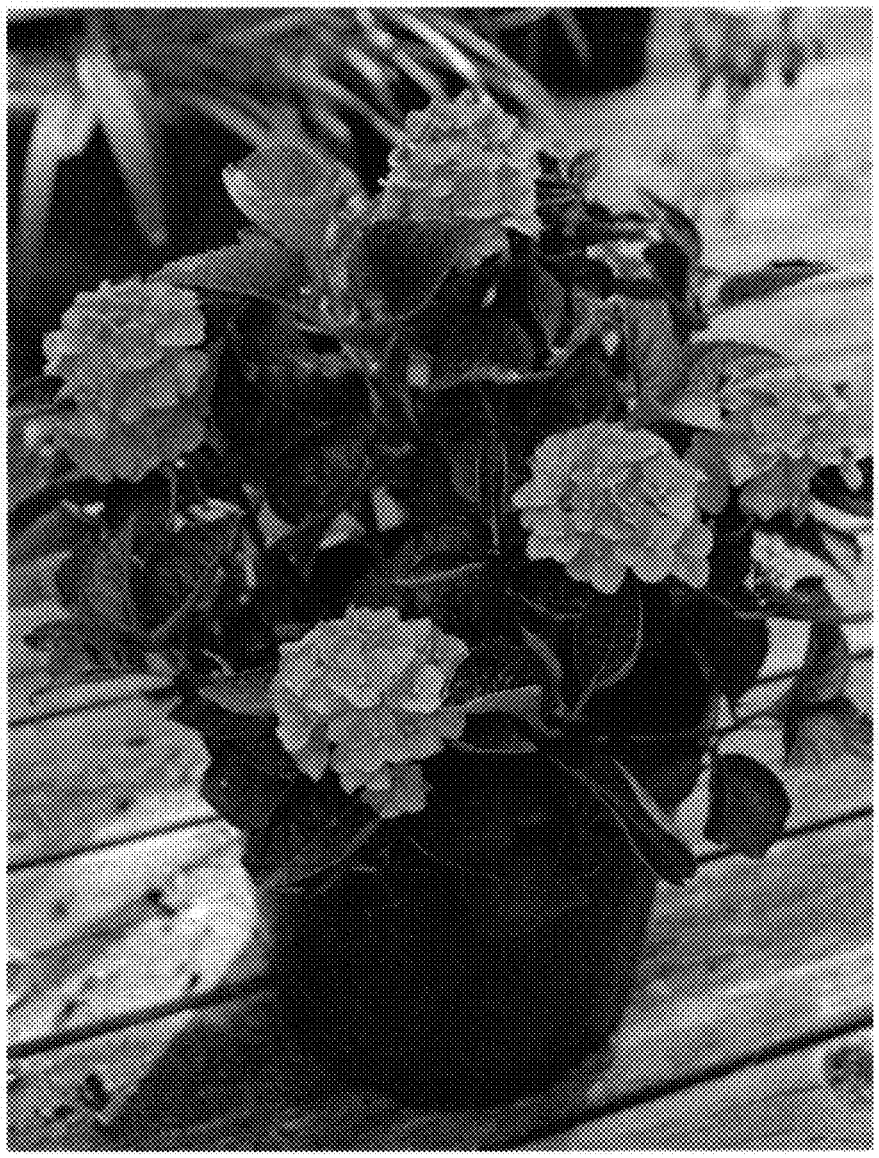
Figure 2:
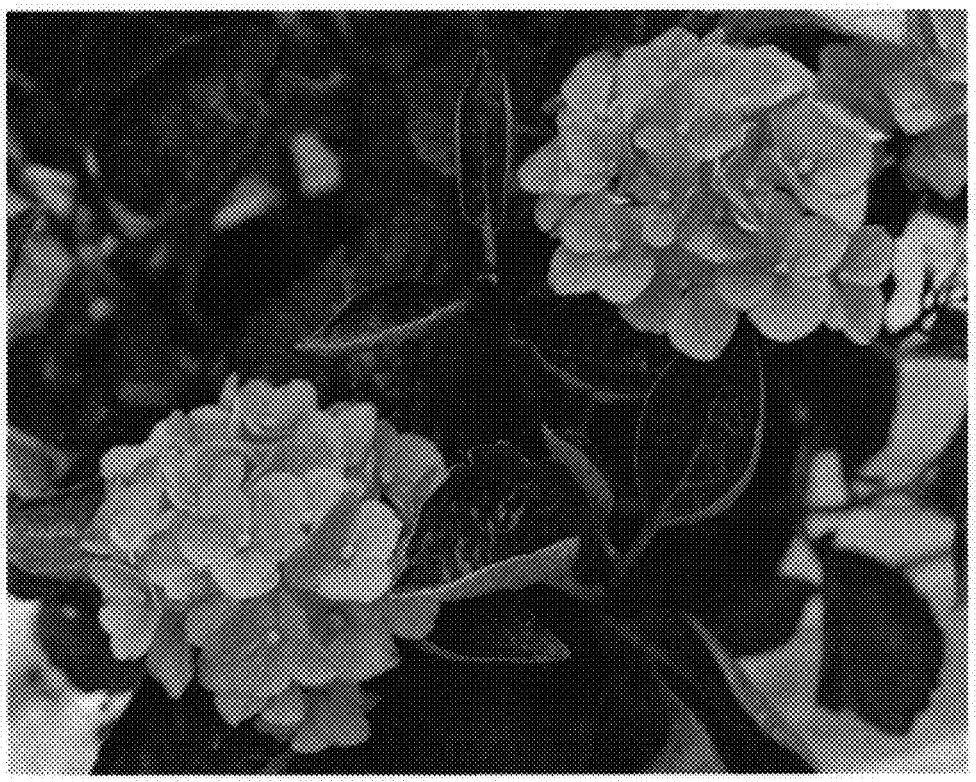

The photograph in FIG. 2 provides a close-up view of inflorescences of 'Hortmavi'.

Figure 3:
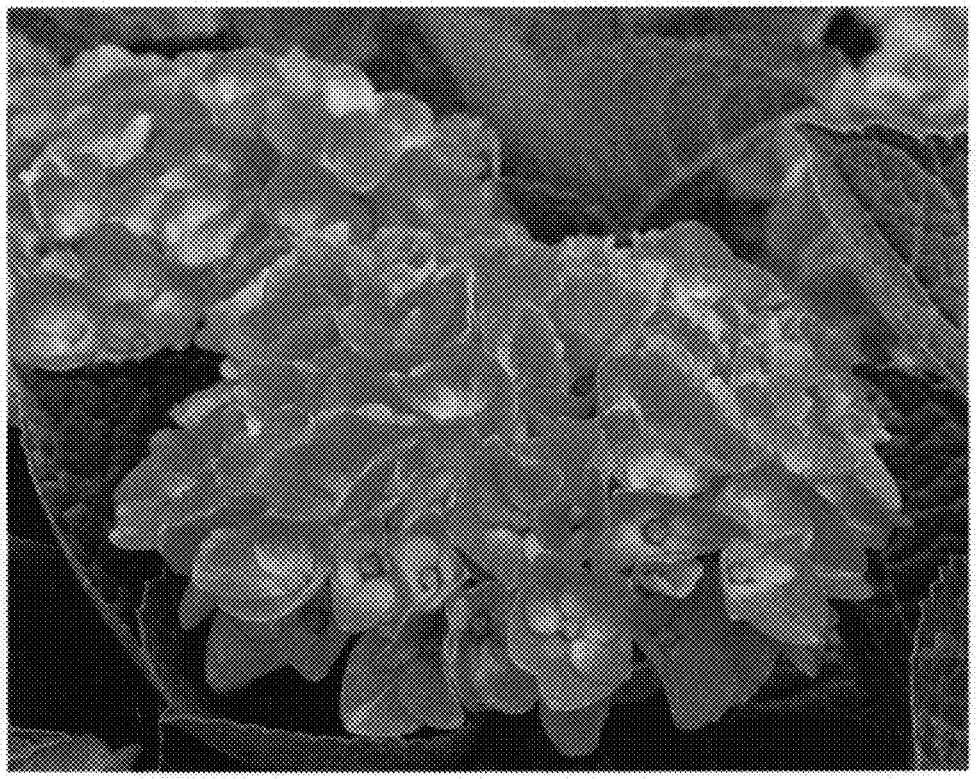

The photograph in FIG. 3 provides a close-up view an opening inflorescence of 'Hortmavi'.

The colors in the photographs are as close as possible with the photographic and printing technology utilized and the color values cited in the Detailed Botanical Description accurately describe the colors of the new *Hydrangea.*

DETAILED BOTANICAL DESCRIPTION

The following is a detailed description of two-year-old plants of 'Hortmavi' as grown in a greenhouse in 3-gallon containers in Visalia, Calif. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period.*—From May to July in a greenhouse and from July to September when grown outdoors in the Netherlands.

*Plant type.*—Deciduous shrub, mophead type *Hydrangea.*

*Plant habit.*—Broad upright, compact.

*Height and spread.*—An average of 32 cm in in height and 36 cm in spread as grown in a 3-gallon container, reaches an average of 1 m in height and width after 3 years in the garden.

*Hardiness.*—At least U.S.D.A. Zones 5 to 9.

*Diseases resistance.*—No susceptibility and resistance has been observed.

*Root description.*—Fine and fibrous, 161C in color.

*Propagation.*—Stem cuttings.

*Root development.*—An average of 3 weeks for root initiation with a young rooted plant produced in an average of six weeks.

*Growth rate and vigor.*—Moderate.

Stem description:

*Stem shape.*—Oval, no fasciation present.

*Stem strength.*—Very strong.

*Stem color.*—Young and mature growth; 144A to 144B slightly suffused with N187C at some nodes, woody bark; a blend of 161B, N199D and 200A.

*Stem size.*—An average of 21 cm in length and 5 mm in diameter.

*Stem surface.*—Glabrous and satiny, sparsely to moderately lenticellate, lenticels; 4 per $cm^2$, an average of 2 mm in length and 1 mm in width, 187A in color, bark; moderately fissured.

*Stem aspect.*—Held primarily upright.

*Internode length.*—An average of 5.2 cm.

*Branching.*—Freely branching with an average of 17 lateral branches.

Foliage description:

*Leaf shape.*—Ovate to elliptic.

*Leaf arrangement.*—Opposite.

*Leaf division.*—Simple.

*Leaf base.*—Obtuse to broad cuneate.

*Leaf apex.*—Broad apiculate.

*Leaf margins.*—Serrate.

*Leaf venation.*—Pinnate, color; upper surface 144A and lower surface 144B blending into 138B towards the outer portion of leaf blade.

*Leaf size.*—An average of 8.2 cm in length and 5.5 cm in width.

*Leaf attachment.*—Petiolate.

*Leaf number.*—An average of 8 per lateral stem.

*Leaf surface.*—Both surfaces; glabrous and slightly rugose, young leaves satiny on upper surface and dull on lower surface, mature leaves dull on both surfaces.

*Leaf color.*—Young foliage; upper surface 146A and lower surface 146B, mature foliage; upper surface NN137A, lower surface 138A.

*Petioles.*—An average of 3.5 cm in length and 3.7 mm in diameter, 144B in color, surface glabrous and satiny to glossy.

Inflorescence description:

*Inflorescence type.*—Terminal panicle, flattened mophead in form comprised of a single sterile flowers above fertile flowers.

*Lastingness of inflorescence.*—Sterile flowers; persistent for an average of 5 weeks, fertile flowers; an average of 5 days, self-cleaning.

*Inflorescence number.*—One per lateral stem.

*Inflorescence size.*—Up to 8 cm in height and 12 cm in diameter.

*Flower number.*—An average of 60 sterile flowers and 25 fertile flowers per panicle.

*Flower fragrance.*—None.

*Flower aspect.*—Upright to very slightly outward.

*Flower size.*—Sterile flowers; an average of 2.8 cm in diameter and 1.5 cm in depth, fertile flowers; an average of 4 mm in diameter and depth.

*Flower type.*—Rotate.

*Flower buds.*—Sterile flowers; an average of 5.5 mm in length and 4 mm in diameter, ovate in shape, N144D in color, fertile flowers; an average of 4 mm in length and 3 mm in diameter, broad obovate in shape, 144C in color at base, upper portion a blend of 70C and 144D.

*Peduncles*.—Primary peduncle; very strong, flattened oval in shape, an average of 4.5 cm in length and 4 mm in width, 147B in color and suffused with 187A and 187B, dull surface is sparsely covered with short soft hairs an average of 0.5 mm in length and 157D in color, lenticels; an average of 6, N77A in color, an average of 3 mm in length and 1 mm in width, secondary peduncles; very strong, an average of 1.2 cm in length and 1.5 mm in width, primarily glabrous (very few short hairs), 147B in color.

*Pedicels*.—Sterile flowers; held primarily at an average angle of 45° from peduncle, an average of 1.6 cm in length and 1.75 mm in diameter, strong strength, color; a blend of 59B and 59C in color, sparsely lenticellate; lenticels an average of 1 mm in length and 0.5 mm in width, an average of 3 per pedicel, 59A in color, dull and very slightly pubescent surface, fertile flowers; held at an average angle of 25° from vertical, an average of 4.5 mm in length and 1.5 mm in diameter, moderate strength, a blend of N77A and N77B in color, glabrous surface.

*Petals*.—Sterile flowers; an average of 4, rotate arrangement but remain closed as a petal spot, acute apex, cuneate base, entire margins, elliptic and concave in shape, an average of 4 mm in length and 2 mm in width, both surfaces; glabrous and dull, color; upper and lower surfaces when opening 149B, upper and lower surfaces when fully opened 68B to 68C, color not fading, fertile flowers; an average of 5, rotate in arrangement, ovate and concave in shape, entire margin, acute to rounded apex, cuneate base, an average of 4 mm in length and 3 mm in width, upper and lower surface glabrous and dull, color; upper and lower surface when opening a blend of 144D and N77B, color when fully open a blend of N77A and N77B in color, shed quickly.

*Sepals*.—Sterile flowers; 5 occasionally 4, rotate arrangement, overlapping, acute-rounded apex with minute notch, broadly cuneate base, entire margins, broadly ovate and concave in shape, an average of 1.6 cm in length and width, both surfaces; glabrous and dull, color; upper and lower surfaces when opening 149A to 149C with apices becoming suffused with 67A and then 68A with marking near the base of 155B, upper surface when fully opened; a blend of 68A and 68B with occasional markings of 144A, lower surface when fully opened; a blend of 68B and 68C with veins 68A and occasional markings of 144A, both surfaces fade to a blend of 68C and 68D and heavily tinged with 152A, fertile flowers; an average of 5, rotate in arrangement, ovate in shape, entire margin, acute apex, truncate base, an average of 2 mm in length and 1 mm in width, both surfaces are glabrous and dull, color; upper and lower surface when opening 144C and when fully opened a blend of 144A and 137C, color not fading.

Reproductive organs:

*Presence*.—Observed on fertile flowers only, if present on sterile flowers, they are not exposed as petals remained closed.

*Stamens*.—An average of 8, anther; broad kidney-shaped, an average of 0.75 mm in length and 158D in color, filament; an average of 2.5 mm in length and 137A in color, pollen was not present.

*Pistils*.—1, 3-lobed, 2.5 mm in length and width, stigmas; club-shaped and N77C in color, styles; an average of 2 mm in length and a blend of 70C and 70B in color, ovary is 145B in color.

*Fruit and seed*.—None observed to date.

It is claimed:

1. A new and distinct cultivar of *Hydrangea* plant named 'Hortmavi' as herein illustrated and described.

* * * * *